(12) United States Patent
Tolley et al.

(10) Patent No.: US 10,598,637 B2
(45) Date of Patent: Mar. 24, 2020

(54) AUTOMATED THERMAL DESORPTION SYSTEMS CONFIGURED TO DETERMINE SAMPLE TUBE ORIENTATION AND/OR CAP PRESENCE, AND RELATED METHODS

(71) Applicant: PerkinElmer Health Sciences, Inc., Waltham, MA (US)

(72) Inventors: Samuel Tolley, Hamden, CT (US); Andrew Tipler, Trumbull, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 124 days.

(21) Appl. No.: 15/653,173

(22) Filed: Jul. 18, 2017

(65) Prior Publication Data
US 2019/0025263 A1    Jan. 24, 2019

(51) Int. Cl.
*G01N 30/32*  (2006.01)
*G01N 1/22*  (2006.01)
(Continued)

(52) U.S. Cl.
CPC ........... *G01N 30/32* (2013.01); *G01N 1/2214* (2013.01); *G01N 35/0099* (2013.01);
(Continued)

(58) Field of Classification Search
CPC ....... G06K 7/1456; G06K 2019/06253; G06K 7/10861; G06K 7/10871; G01K 7/015;
(Continued)

(56) References Cited

U.S. PATENT DOCUMENTS 5,369,713 A * 11/1994 Schwartz ............. B07C 5/3408
  348/86
5,948,360 A   9/1999 Rao et al.
(Continued)

FOREIGN PATENT DOCUMENTS

AU    2015261711    12/2015
CN    201586636 U    9/2010
(Continued)

OTHER PUBLICATIONS

Markes International "Multi-function TD autosampler with internal standard addition Series 2 Ultra Thermal Desorption Autosampler" brochure (12 pages) (Date Unknown).
(Continued)

*Primary Examiner* — Lisa M Caputo
*Assistant Examiner* — Tran M. Tran
(74) *Attorney, Agent, or Firm* — Myers Bigel, P.A.

(57) ABSTRACT

According to embodiments of the technology, an automated thermal desorption system includes a sample tube including a chamber to contain an analyte, visible indicia on the sample tube, a thermal desorption apparatus, and a sample tube monitoring system. The thermal desorption apparatus is configured to receive the sample tube and includes a heating device. The heating device is configured to heat the sample tube in the thermal desorption apparatus and thereby desorb the analyte from the sample tube. The sample tube monitoring system includes: an optical sensor configured to read the visible indicia on the sample tube and to generate an output signal corresponding thereto; and a controller configured to receive the output signal corresponding to the visible indicia from the optical sensor and to determine an orientation of the sample tube with respect to the thermal desorption apparatus based on the output signal.

28 Claims, 6 Drawing Sheets

(51) Int. Cl.
*G01N 35/00* (2006.01)
*G01N 35/04* (2006.01)
*G01N 30/02* (2006.01)
*G01N 30/12* (2006.01)
*G01N 30/88* (2006.01)

(52) U.S. Cl.
CPC ....... *G01N 35/04* (2013.01); *G01N 2030/025* (2013.01); *G01N 2030/128* (2013.01); *G01N 2030/324* (2013.01); *G01N 2030/8881* (2013.01); *G01N 2035/00752* (2013.01); *G01N 2035/0441* (2013.01); *G01N 2035/0491* (2013.01)

(58) Field of Classification Search
CPC ........ G01N 30/06; G01N 30/72; G01N 30/86; G01N 30/6004; G01N 2030/6013; G01N 35/00732; G01N 2035/00752; H01J 49/049; H01J 49/0413; B67B 7/182
See application file for complete search history.

(56) References Cited

U.S. PATENT DOCUMENTS

| | | | |
|---|---|---|---|
| 6,167,767 B1 | 1/2001 | Mengel et al. | |
| 6,244,117 B1 | 6/2001 | Mengel et al. | |
| 6,246,642 B1* | 6/2001 | Gardner, Jr. | G11B 15/682 369/30.42 |
| 6,251,267 B1* | 6/2001 | Allington | B01D 11/0203 210/143 |
| 6,272,937 B1* | 8/2001 | Mengel | G01N 1/2273 422/64 |
| 6,321,609 B1* | 11/2001 | Mengel | G01N 1/2273 73/863.21 |
| 6,340,588 B1* | 1/2002 | Nova | B01J 19/0046 435/287.1 |
| 6,446,515 B2 | 9/2002 | Cole et al. | |
| 6,465,770 B2* | 10/2002 | Gseller | G01N 35/04 250/221 |
| 6,722,564 B2* | 4/2004 | Creager | G11B 15/6835 235/383 |
| 6,871,566 B2* | 3/2005 | Niwayama | B67B 7/182 53/381.4 |
| 7,662,630 B2 | 2/2010 | Tipler et al. | |
| 7,988,933 B2* | 8/2011 | Vijay | B01L 9/06 422/119 |
| 8,043,561 B2* | 10/2011 | Yamakawa | G01N 35/00594 422/63 |
| 8,100,266 B2* | 1/2012 | Lackner | G01N 35/0099 209/518 |
| 8,170,271 B2* | 5/2012 | Chen | G01N 35/00732 382/100 |
| 8,252,232 B2* | 8/2012 | Neeper | G01N 35/00732 422/65 |
| 8,859,289 B2* | 10/2014 | Marty | G01N 35/00732 422/65 |
| 8,864,030 B2* | 10/2014 | Ohmae | G01N 35/00732 235/462.01 |
| 9,040,288 B2* | 5/2015 | Handique | B01L 3/5027 435/288.5 |
| 9,057,714 B2* | 6/2015 | Gomm | G01N 35/025 |
| 9,092,650 B2* | 7/2015 | Pronkine | G06K 9/00 |
| 9,135,487 B2* | 9/2015 | Itoh | G06K 7/10831 |
| 9,151,770 B2* | 10/2015 | Reuteler | G01N 35/0099 |
| 9,236,236 B2* | 1/2016 | DeWitte | G01N 30/06 |
| 9,251,393 B2 | 2/2016 | Pollack | |
| 9,446,418 B2* | 9/2016 | Johns | B01D 21/262 |
| 9,835,640 B2* | 12/2017 | Raicu | B65G 1/06 |
| 9,910,054 B2* | 3/2018 | Johns | B01D 21/262 |
| 9,953,820 B2* | 4/2018 | Piper | G01N 1/02 |
| 10,012,661 B2* | 7/2018 | Pollack | G06K 7/10861 |
| 10,088,460 B2* | 10/2018 | DeWitte | G01N 30/06 |
| 10,191,072 B2* | 1/2019 | Gomm | G01N 35/025 |
| 10,247,743 B2* | 4/2019 | Suzuki | G01N 33/491 |
| 10,274,505 B2* | 4/2019 | Johns | B01D 21/262 |
| 2002/0074405 A1* | 6/2002 | Hadano | G06K 7/10851 235/462.08 |
| 2008/0041137 A1 | 2/2008 | Tipler et al. | |
| 2008/0121688 A1* | 5/2008 | Harrop | G06K 19/06028 235/375 |
| 2013/0000485 A1 | 1/2013 | Tipler et al. | |
| 2016/0245730 A1 | 8/2016 | Neal | |
| 2017/0269112 A1* | 9/2017 | Gerstel | B04B 5/0414 |
| 2018/0100868 A1* | 4/2018 | Grimwood | B01L 3/5023 |
| 2018/0106820 A1* | 4/2018 | Okabe | G01N 35/02 |
| 2018/0239936 A1* | 8/2018 | Kluckner | G06K 9/629 |
| 2018/0252737 A1* | 9/2018 | Gemperle | G01N 35/00732 |
| 2019/0041318 A1* | 2/2019 | Wissmann | G01N 21/253 |

FOREIGN PATENT DOCUMENTS

| | | |
|---|---|---|
| EP | 2921859 | 9/2015 |
| WO | 2014/045057 | 3/2014 |

OTHER PUBLICATIONS

Markes International "TubeTAG$^{PLUS}$TM" Operator's Manual (15 pages) (Oct. 2009).
PerkinElmer, Inc. "TurboMatrix Series Thermal Desorbers" User's Guide (422 pages) (Jan. 2007).
"TurboMatrix Headspace Sampler and HS 40/110 Trap User's Guide" PerkinElmer, Inc. (357 pages) (Feb. 2008).
Notification of Transmittal of the International Search Report and the Written Opinion of the International Searching Authority, or the Declaration, in corresponding PCT Application No. PCT/US2018/038063 (15 pages) (dated Oct. 1, 2018).

* cited by examiner

AUTOMATED THERMAL DESORPTION SYSTEMS CONFIGURED TO DETERMINE SAMPLE TUBE ORIENTATION AND/OR CAP PRESENCE, AND RELATED METHODS

FIELD

The present technology relates to thermal desorption apparatus and methods and, more particularly, to automated thermal desorption apparatus and methods.

BACKGROUND

Gas chromatography is essentially a physical method of separation in which constituents of a vapor sample in a carrier gas are adsorbed or absorbed and then desorbed by a stationary phase material in a column. Interactions between this stationary phase material and the various components of the sample—which differ based upon differences among partition coefficients of the components—cause the sample to be separated into the respective components. At the end of the column, the individual components are more or less separated in time. Detection of the gas provides a time-scaled pattern, typically called a chromatogram, that, by calibration or comparison with known samples, indicates the constituents, and the specific concentrations thereof, which are present in the test sample. An example of the process by which this occurs is described in U.S. Pat. No. 5,545,252 to Hinshaw.

Often, the analytes to be measured are retained by and concentrated on an adsorbent in a sample tube. Once the analytes are collected in the sample tube, the tube is then transported to a thermal desorption unit, where the tube is placed in the flow path of an inert gas, such as helium or nitrogen. The tube is subsequently heated, thereby desorbing the analytes, and the carrier gas sweeps the analytes out of the tube. In some cases, a trap is located downstream of the sample tube in order to further pre-concentrate the analytes, and occasionally, remove moisture therefrom, prior to introducing the sample into the chromatographic column. One example of such a trap is an adsorbent trap, usually cooled to a sub-ambient temperature, which may simply be another sorbent tube with a suitable adsorbent material. The adsorbent trap adsorbs the analytes as the sample gas first passes through the tube. The analytes are then subsequently desorbed into the chromatographic column from the trap, usually by heating, for subsequent separation and analysis as discussed above. Typically, either the column is directly coupled to a sorbent tube in the thermal desorption unit or the unit is connected directly to the column via a transfer line, such as, for example, via a length of fused silica tubing.

One common application of chromatographic analysis using a thermal desorption unit is to determine the constituents of a particular environment. For example, it is often desired to detect the amount of volatile organic compounds (VOCs) present in a certain sample of air. One way of doing this is by first transporting a sample tube packed with an adsorbent material into the environment to be tested, and allowing the VOCs in the air to migrate into the tube through natural diffusion, typically termed "diffusive" or "passive sampling." Alternatively, the VOCs may be collected by drawing a sample of gas (typically ambient air) through such a tube using a small vacuum pump, commonly referred to as "pumped sampling." In each case, the analytes to be measured (i.e., the VOCS) are retained by and concentrated on the adsorbent as the air passes through the tube.

Once the VOCs are collected in this fashion, the sample tube is then transported to the thermal desorption unit, where the tube is placed in the flow path of an inert gas, such as helium or nitrogen. The sample tube is subsequently heated, thereby desorbing the analytes, and the carrier gas sweeps the VOCs out of the tube and into a second trap, typically cooled to sub-ambient temperatures, or the chromatographic column. Typically, either the chromatographic column is directly coupled to a sorbent tube or the sub-ambient trap in the thermal desorption unit or the unit is connected directly to the column via a transfer line, such as, for example, via a length of fused silica tubing.

Some thermal desorption apparatus are automated thermal desorption apparatus or units that automate the processing and handling of sample tubes. For example, the TurboMatrix 650 ATD available from PerkinElmer is an automated analytical thermal desorber including a carousel, a robot arm, a capping/decapping station, and a sampling station. In use, the robot arm automatically collects a sample tube from the carousel and transports the sample tube to the capping/decapping station where end caps are removed from the sample tube. The robot arm then places the uncapped sample tube in the sampling station. In the sampling station, the sample tube is heated to desorb an analyte from the sample tube as described above. Thereafter, the robot arm returns the sample tube to the capping/decapping station (where the sample tube is recapped) and then the carousel.

SUMMARY

According to embodiments of the technology, an automated thermal desorption system includes a sample tube including a chamber to contain an analyte, visible indicia on the sample tube, an automated thermal desorption device, and a sample tube monitoring system. The automated thermal desorption device is configured to receive the sample tube and includes a heating device. The heating device is configured to heat the sample tube in the automated thermal desorption device and thereby desorb the analyte from the sample tube. The sample tube monitoring system includes: an optical sensor configured to read the visible indicia on the sample tube to generate an output signal corresponding thereto; and a controller configured to receive the output signal corresponding to the visible indicia from the optical sensor and to determine an orientation of the sample tube with respect to the automated thermal desorption device based on the output signal.

In some embodiments, the visible indicia is a barcode. According to some embodiments, the barcode is substantially permanently located on the sample tube. The barcode may be substantially permanently printed, etched or embossed on the sample tube.

In some embodiments, the controller is configured to programmatically and automatically determine whether the sample tube is not oriented in a prescribed orientation with respect to the automated thermal desorption device.

In some embodiments, the sample tube monitoring system is configured to: determine that the sample tube is not oriented in a prescribed orientation with respect to the automated thermal desorption device; and in response to determining that the sample tube is not oriented in the prescribed orientation, issue an alert and/or automatically stop processing of the sample tube by the automated thermal desorption device.

According to some embodiments, the automated thermal desorption device includes an outlet conduit and a sampling station configured to receive the sample tube such that the chamber is fluidly connected to the outlet conduit and the sample tube is positioned to be heated by the heating device, and the sample tube monitoring system is configured to read the visible indicia using the optical sensor when the sample tube is in the sampling station and to determine therefrom an orientation of the sample tube with respect to the sampling station. In some embodiments, the automated thermal desorption device further includes an inlet conduit fluidly connected to a supply of a carrier gas, and the sampling station is configured to receive the sample tube such that the chamber is fluidly connected to the inlet conduit to direct a flow of the carrier gas from the inlet conduit, through the chamber and into the outlet conduit.

In some embodiments, the automated thermal desorption device includes a sample tube holder configured to hold a plurality of sample tubes, and the sample tube monitoring system is configured to read the visible indicia using the optical sensor when the sample tube is in the sample tube holder and to determine therefrom an orientation of the sample tube with respect to the automated thermal desorption device. The sample tube holder may be a rotatable carousel.

According to some embodiments, the automated thermal desorption device includes an outlet conduit, a sampling station, and a tube transport system. The sampling station is configured to receive the sample tube such that the chamber is fluidly connected to the outlet conduit and the sample tube is positioned to be heated by the heating device. The tube transport system includes a robot arm. The tube transport system is configured to collect and move the sample tube to the sampling station using the robot arm. The optical sensor is mounted on the robot arm.

In some embodiments, the automated thermal desorption system includes an end cap mounted on the sample tube and selectively removable from the sample tube, wherein the sample tube monitoring system is configured to acquire an image of the sample tube using the optical sensor and to determine therefrom whether the end cap is mounted on the sample tube. In some embodiments, the sample tube monitoring system is configured to issue an alert and/or automatically stop processing of the sample tube by the automated thermal desorption device based on a determination by the sample tube monitoring system that the end cap is not mounted on the sample tube. According to some embodiments, the automated thermal desorption device includes a decapping station configured to remove the end cap from the sample tube, and the sample tube monitoring system is configured to, in response to determining that the end cap is not mounted on the sample tube, issue an alert and/or automatically stop the automated thermal desorption device from attempting to remove the end cap from the sample tube using the decapping station.

In some embodiments, the automated thermal desorption system includes a gas chromatograph fluidly connected to the automated thermal desorption device to receive and detect the desorbed analyte from the automated thermal desorption device.

According to embodiments of the technology, a method for desorbing an analyte from a sample tube includes: providing a sample tube including a chamber containing an analyte, wherein visible indicia is disposed on the sample tube; placing the sample tube in an automated thermal desorption device, the automated thermal desorption device including a heating device that is configured to heat the sample tube in the automated thermal desorption device and thereby desorb the analyte from the sample tube; and reading the visible indicia using an optical sensor of a sample tube monitoring system and determining an orientation of the sample tube with respect to the automated thermal desorption device based on the visible indicia.

According to embodiments of the technology, an automated thermal desorption system includes: a sample tube including a chamber to contain an analyte; an end cap mounted on the sample tube and selectively removable from the sample tube; visible indicia on the sample tube; an automated thermal desorption device; and a sample tube monitoring system. The automated thermal desorption device is configured to receive the sample tube and including a heating device. The heating device is configured to heat the sample tube in the automated thermal desorption device and thereby desorb the analyte from the sample tube. The sample tube monitoring system includes: an optical sensor configured to acquire an image of the sample tube; and a controller configured to receive image data corresponding to the acquired image from the optical sensor and to determine whether the end cap is mounted on the sample tube based on the acquired image.

In some embodiments, the automated thermal desorption system includes a second end cap mounted on an end of the sample tube opposite the first end cap and selectively removable from the sample tube, and the controller is configured to determine whether the second end cap is mounted on the sample tube based on the acquired image.

According to embodiments of the technology, a method for desorbing an analyte from a sample tube includes: providing a sample tube including a chamber containing an analyte, wherein visible indicia is disposed on the sample tube; placing the sample tube in an automated thermal desorption device, the automated thermal desorption device including a heating device that is configured to heat the sample tube in the automated thermal desorption device and thereby desorb the analyte from the sample tube; and reading the visible indicia using an optical sensor of a sample tube monitoring system and determining whether an end cap is mounted on the sample tube based on the acquired image.

Further features, advantages and details of the present technology will be appreciated by those of ordinary skill in the art from a reading of the figures and the detailed description of the preferred embodiments that follow, such description being merely illustrative of the present technology.

DETAILED DESCRIPTION

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present technology.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

The term "automatically" means that the operation is substantially, and may be entirely, carried out without human or manual input, and can be programmatically directed or carried out.

The term "programmatically" refers to operations directed and/or primarily carried out electronically by computer program modules, code and/or instructions.

The term "electronically" includes both wireless and wired connections between components.

With reference to the figures, a sample analyzer system 10 according to some embodiments of the technology is schematically shown therein. The sample analyzer system 10 includes an automated thermal desorption (ATD) system 101, a gas chromatography (GC) system 20, and a controller 50. The ATD system 101 includes an automated thermal desorption (ATD) device 100 and one or more sample tube assemblies 160.

Figure 1:
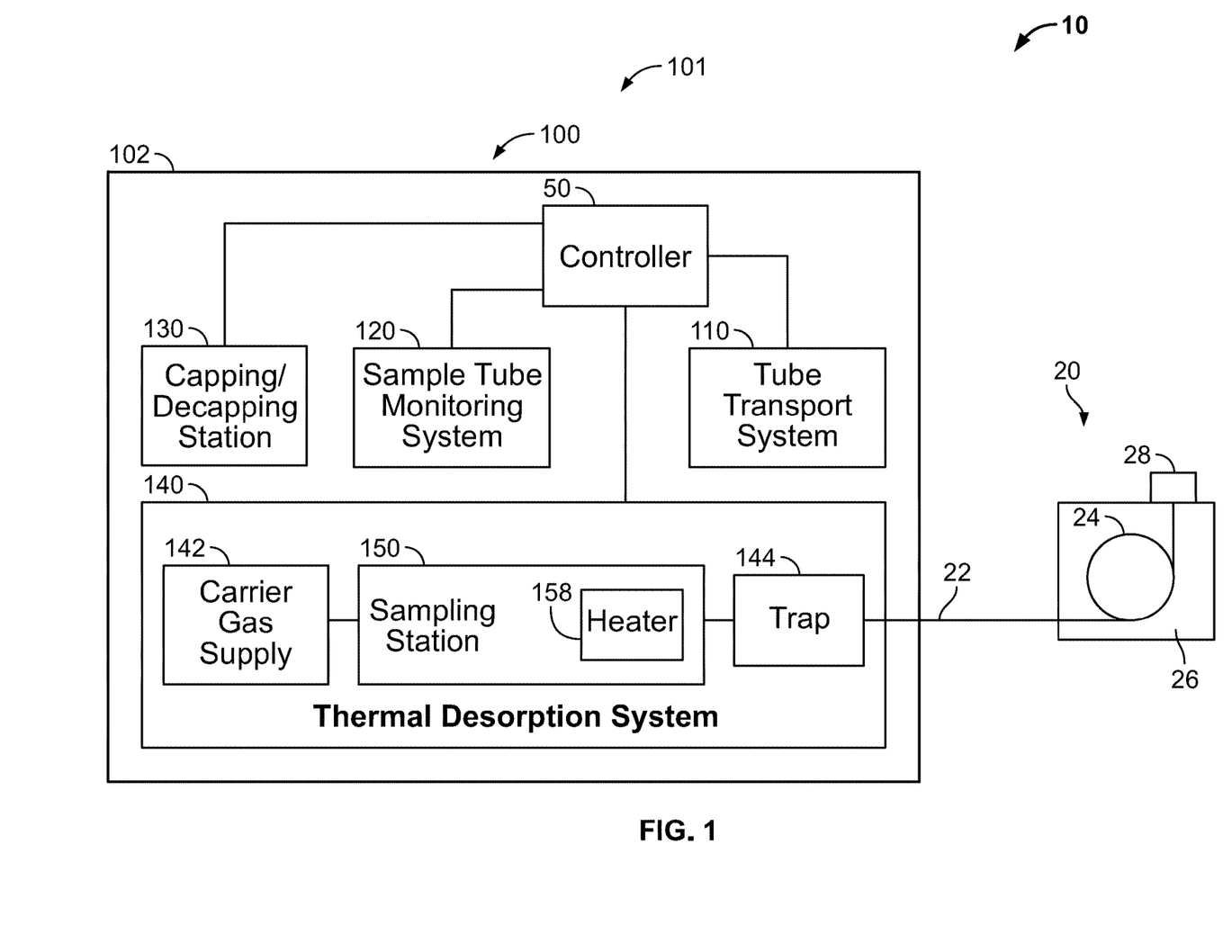
FIG. 1 is schematic representation of a sample analyzer system according to embodiments of the technology.

The GC system 20 may be any suitable GC apparatus. With reference to FIG. 1, an exemplary GC system 20 includes a sample feed line 22, a column 24, a heater or oven 26 and a detector 28. In use, a carrier gas (the mobile phase; e.g., helium or nitrogen) sweeps a sample from the ATD device 100 through the feed line 22 to an inlet of the column 24, and through the column 24 to the detector 28, and thereafter to waste collection, a further detector or other desired destination. The oven 26 selectively heats the column 24 before, during and/or after the sample is passed therethrough in order to control the temperature of the column 24 and the sample. The column 24 includes an inner layer or packing of a selected stationary phase in or on the inner wall of the column 24. The gaseous compounds of the sample interact with the stationary phase; having a different affinity for each component, retains the different components of the sample for different times. As a result, the different compounds elute at different times and take different amounts of time to pass through and exit the column 24 to the detector 28 (i.e., the components have different retention times within the column 24). The detector 28 monitors the outlet stream from the column 24 to detect or sense the time at which each analyte component emerges from the column 24 and reaches the detector 28, and/or the amount of the analyte. The detection data from the detector 28 may be stored by a recorder. Various parameters of the process may be controlled by the controller 50, including the carrier gas flow rate (using a flow controller), the column and/or mobile phase temperatures (using the GC oven 26), and the sample injection timing and rate.

With reference to FIGS. 1-4, the ATD device includes a support frame 102, a sample tube handling or transport system 110, a sample tube monitoring system 120, a capping/decapping station 130, and a thermal desorption (TD) system 140. The TD system 140 includes a carrier gas supply 142, a sampling station 150, and a trap 144.

Figure 2:
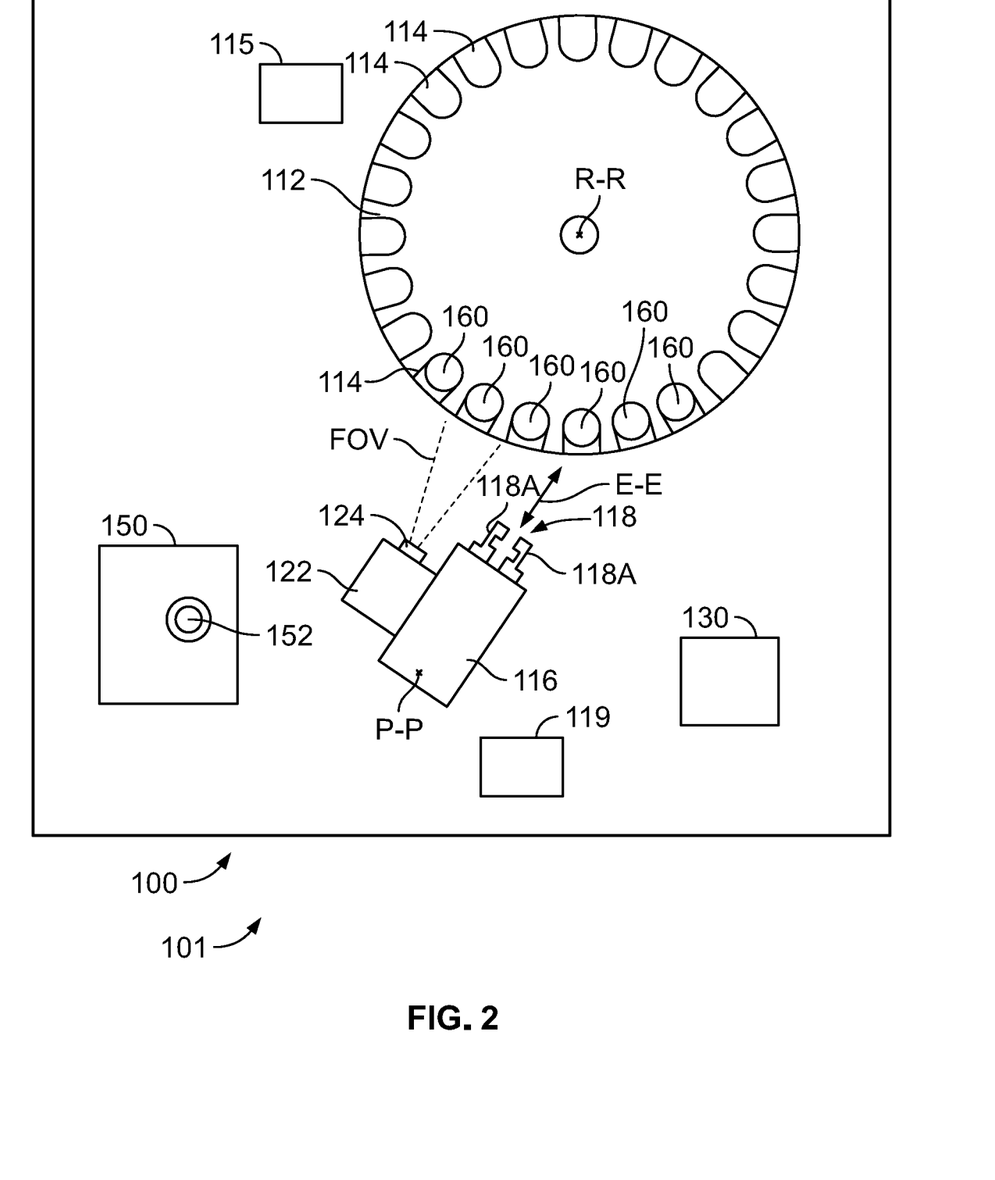
FIG. 2 is a top view of an automated thermal desorption (ATD) system forming a part of the sample analyzer system of FIG. 1.
Figure 3:
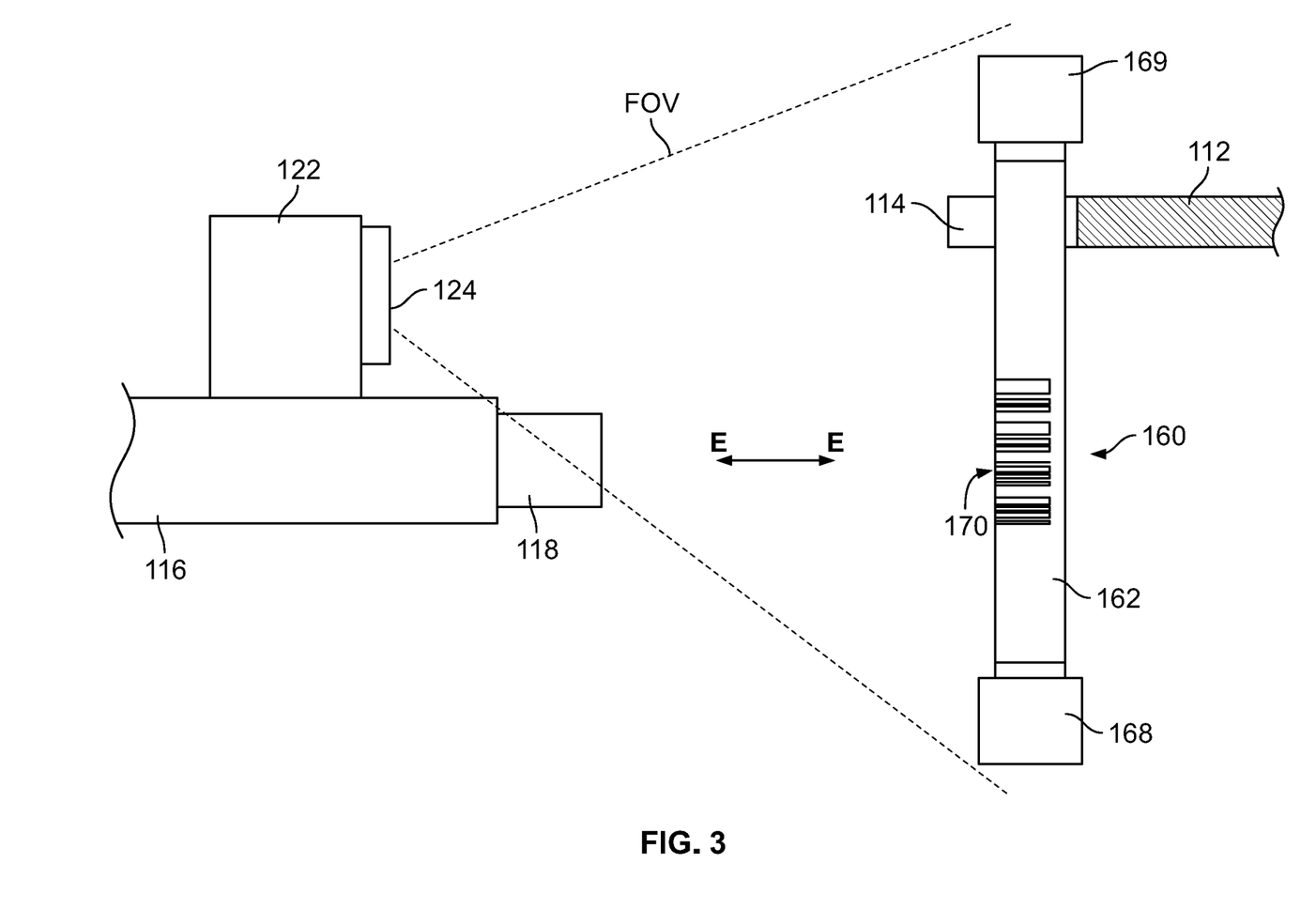
FIG. 3 is a fragmentary, side view of the ATD system of FIG. 2.

With reference to FIGS. 2 and 3, the sample tube transport system 110 includes a sample tube holder (in the form of a carousel sample tray 112) mounted on the frame 102 for rotation about a rotation axis R-R. Sample tube holding receptacles or slots 114 are provided in the carousel tray 112 and are each configured to receive and releasably hold a sample tube assembly 160 for storage and transport. A carousel actuator 115 (e.g., one or more electric motors) is provided to drive rotation of the carousel 112 under control of the controller 50, for example.

The sample tube transport system 110 further includes a robot transfer arm 116 mounted on the frame 102, and an end effector or gripper 118 mounted on the arm 116. The arm 116 can pivot about a pivot axis P-P. The gripper 118 can extend and retract (i.e., translate fore and aft) relative to the arm 116 along an extension axis E-E. The gripper 118 includes opposed jaws 118A that can open and close to receive and grasp a sample tube assembly 160. A robot arm actuator 119 (e.g., one or more electric motors) is provided to drive movement of the arm 116 and the gripper 118 under control of the controller 50, for example.

Figure 4:
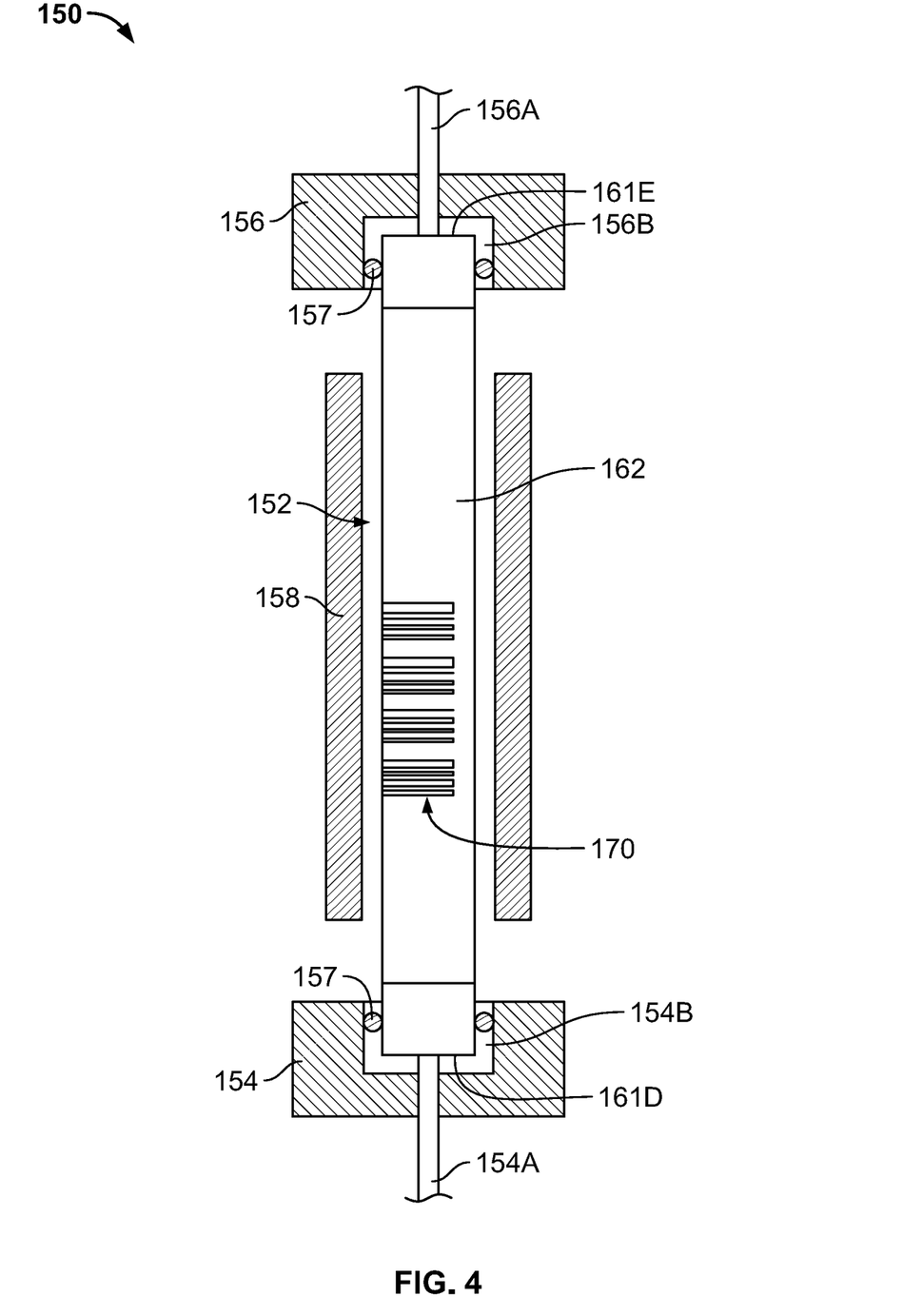
FIG. 4 is a fragmentary, side view of a sampling station forming a part of the ATD system of FIG. 2.

With reference to FIG. 4, the sampling station 150 includes a supply end fixture 154 and an opposing outlet end fixture 156 defining a sample tube receiver slot 152 therebetween. A carrier gas supply conduit 154A fluidly connects the carrier gas supply 142 to the fixture 154. An outlet conduit 156A fluidly connects the fixture 156 to the feed line 22. It will be appreciated that the conduit 154A may not directly connect the carrier gas supply 142 to the fixture 154. One or more valves, conduits or other components may be provided in line between the carrier gas supply 142 and the conduit 154A to control the flow and complete the fluid connection between the carrier gas supply 142 and the fixture 154. Likewise, the conduit 156A may not directly connect the fixture 156 to the feed line 22. One or more valves, conduits or other components may be provided in line between the fixture 156 and the feed line 22 to control the flow and complete the fluid connection between the fixture 156 and the feed line 22.

Tube end receiver bores 154B, 156B are defined in the fixtures 154, 156 and are provided with seals 157 (e.g., O-rings). A sample tube heater 158 is positioned to heat a sample tube in the sample tube receiver slot 152. The sample tube heater 158 may be positioned adjacent to or surrounding a portion of the sample tube receiver slot 152. The sample tube heater 158 may be an electrical resistance heater, for example.

The sample tube monitoring system 120 includes an optical sensor 122. According to some embodiments, the optical sensor 122 is a barcode reader. The barcode reader (or other optical sensor) 122 has an optical reception window 124, which may include a lens. The barcode reader 122 has a field of view FOV as schematically shown in FIGS. 2 and 3. The sample tube monitoring system 120 may include two or more optical sensors 122.

Suitable barcode readers for the optical sensor 122 may include a MicroScan ID20 barcode reader. Other suitable optical sensors for the optical sensor 122 may include a JADAK JE-205 barcode scan engine.

Figure 5:
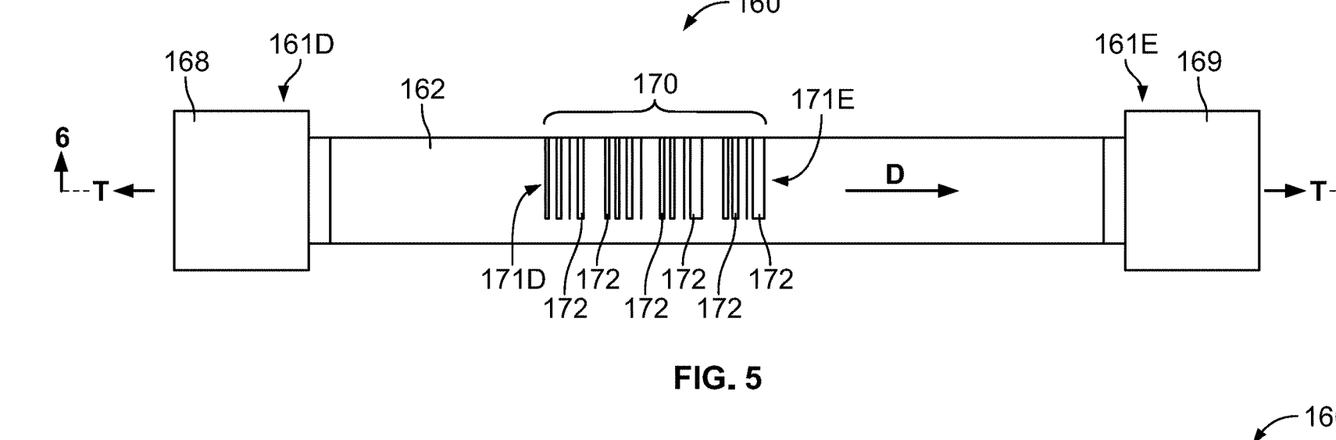
FIG. 5 is a side view of a sample tube assembly forming a part of the ATD system of FIG. 2.
Figure 6:
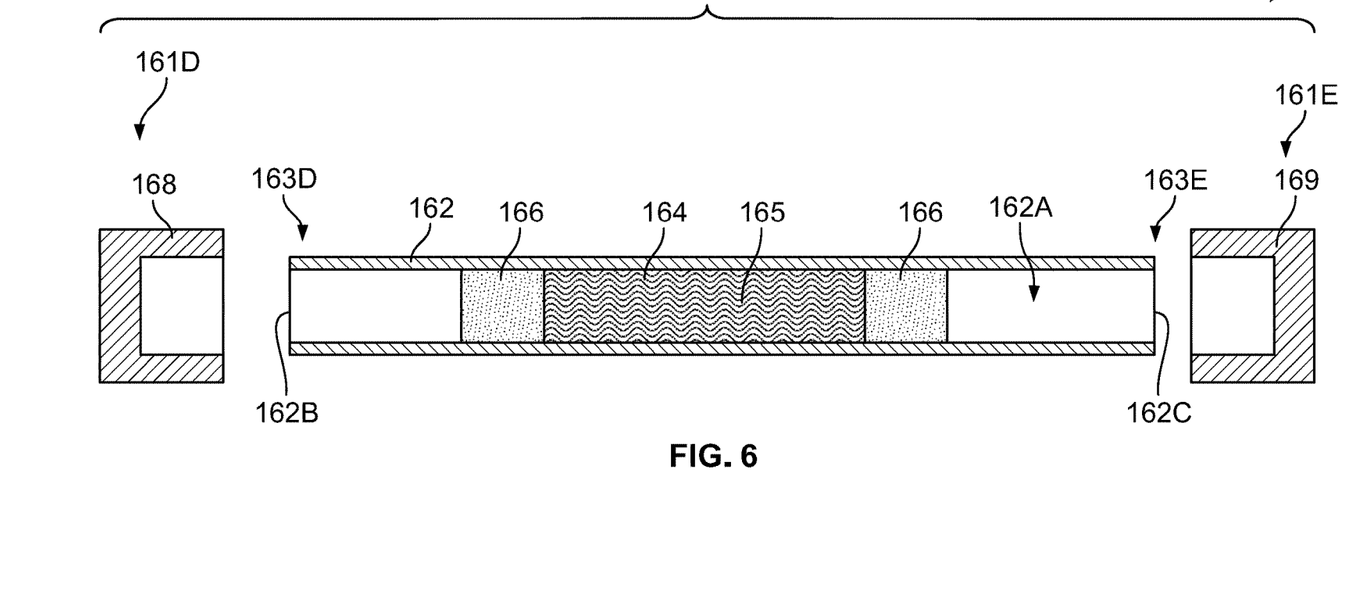
FIG. 6 is an exploded, cross-sectional view of the sample tube assembly of FIG. 5 taken along the line 6-6 of FIG. 5.

An exemplary one of the sample tube assemblies 160 is shown in FIGS. 5 and 6. The sample tube assembly 160 includes a tubular sample tube 162 having a sample tube axis T-T. The sample tube 162 defines a containment chamber, cavity or through passage 162A terminating at an inlet opening 162B and an opposing outlet opening 162C. The sample tube assembly 160 has a prescribed inlet end 161D and a prescribed outlet end 161E spaced apart along the sample tube axis T-T. The sample tube 162 has a prescribed operational direction F extending from the inlet opening 162B and inlet end 161D to the outlet opening 162C and outlet end 161E.

The sample tube 162 may be formed of any suitable material(s). In some embodiments, the sample tube 162 is formed of a material selected from the group consisting of steel or glass.

The sample tube assembly 160 further includes an inlet end cap 168 fluidly sealing the opening 162B and an outlet end cap 169 fluidly sealing the outlet opening 162C. The end caps 168, 169 are removably and replaceably mounted on the inlet end 163D and the outlet end 163E of the sample tube 162.

The end caps 168, 169 may be formed of any suitable material(s). In some embodiments, the end caps 168, 169 are formed of a material selected from the group consisting of polytetrafluoroethylene (PFTE).

The sample tube assembly 160 further includes visible indicia 170 on the sample tube. In some embodiments and as shown in the figures, the visible indicia 170 is a barcode including a plurality of indicia bars 172 distributed along the length of the sample tube 162. The barcode 170 has a prescribed first end 171D and a prescribed second end 171E spaced apart along the sample tube axis T-T. The first end 171D is located proximate the inlet end 163D and the second end 171E is located proximate the outlet end 163E. Thus, the barcode 170 has an orientation corresponding to the orientation of the axis T-T of the sample tube 162.

The barcode (or other visible indicia) 170 may be formed of any suitable material(s) and may be secured to the sample tube 162 by any suitable technique. In some embodiments, the barcode 170 is permanently located (i.e., secured or formed) on the sample tube 162. In some embodiments, the barcode 170 is permanently embossed or etched into a surface (e.g., the outer surface) of the sample tube 162. In some embodiments, the barcode 170 is printed (and, in some embodiments, permanently printed) on a surface (e.g., the outer surface) of the sample tube 162.

In some embodiments, the sample tube assembly 160 includes an adsorbent media 164 disposed in the chamber 162A. The analyte or sample 165 to be desorbed and analyzed may be present (e.g., adsorbed) on and/or in the adsorbent media 164. Retention media 166 may be located in the chamber 162A on one or both ends of the adsorbent media 164 to inhibit movement of the adsorbent media 164 within the chamber 162A.

The adsorbent media 164 may be formed of any suitable material(s). In some embodiments, the adsorbent media 164 is formed of a material selected from the group consisting of activated carbon.

The retention media 166 may be formed of any suitable material(s). In some embodiments, the retention media 166 is formed of a material selected from the group consisting of glass wool.

The carrier gas may be any suitable gas. The carrier gas may include helium, nitrogen, hydrogen or argon, for example.

The controller 50 may be any suitable device or devices for providing the functionality described herein. The controller 50 may include a plurality of discrete controllers that cooperate and/or independently execute the functions described herein. The controller 50 may include a microprocessor-based computer.

The sample analyzer system 10 can be used and operated as follows in accordance with methods of the present technology. The controller 50, the actuators 115, 119, the barcode reader 122, the capping/decapping station 130, the TD system 140, and the GC system 20 collectively serve as a control system operative to execute the methods.

One or more sample tube assemblies 160 are each mounted in a respective one of the slots 114 in the carousel tray 112. Each sample tube assembly 160 and its position in the carousel tray 112 may be identified and registered or indexed in a tube data memory 216A (FIG. 7) associated with the controller 50. Each sample tube assembly 160 has a unique identity that is represented in its barcode 170.

Generally, when it is desired to analyze the sample 165 in a selected sample tube assembly 160, that sample tube assembly 160 is transported by the transport system 110 from the carousel tray 112 to the capping/decapping station 130 where the caps 168, 169 are removed. The decapped sample tube 162 is then transported to the sampling station slot 152 by the transport system 110. The sampling station 150 captures and seals the ends 163D and 163E of the sample tube 162 in the end fixtures 154 and 156, respectively, as shown in FIG. 4. The sampling station 150 then heats the sample tube 162 using the heater 158. The sample 165 is thereby desorbed from the adsorbent media 164 and swept by carrier gas from the supply conduit 154A into the exit conduit 156A. The sample/carrier gas mixture is flowed to the trap 144 where the sample is concentrated. From the trap 144, the sample/carrier gas mixture is flowed through the feed line and into the column 24 of the GC system 20. In the GC system 20, the sample is processed as described above. The sample tube 162 may then be transported to the capping/decapping station 130 where the end caps 168, 169 are reinstalled. The sample tube assembly may then be returned to the carousel tray 112 or placed elsewhere.

The handling of the sample tube 162 and the operation of the sample tube monitoring system 120 will now be described in more detail. It will be appreciated that in some embodiments one or more of the steps discussed below may be omitted.

The controller 50 may rotate the carousel tray 112 to position the target or selected sample tube assembly 160 at a prescribed pickup location proximate the robot arm 116. In the pickup location, the barcode 170 of the sample tube 162 of the selected sample tube assembly 160 is in the field of view FOV of the barcode reader 122. The barcode reader 122 will read the barcode 170 and send an output signal corresponding to the barcode 170 to the controller 50. More particular, in some embodiments, the barcode reader 122 (optical sensor) is configured to generate an electrical output signal having voltage levels in a pattern corresponding to the barcode 170 (visible indicia). The controller 50 is configured to receive and process the output signal. In some embodiments, the output signal represents or embodies image data corresponding to the barcode 170. The output signal will be described hereinbelow with reference to image data; however, in some embodiments, the output signal may represent or embody data other than image data, such as a one dimensional data string.

The controller 50 will process the image data to determine the orientation of the sample tube 162. In some embodiments, the controller 50 programmatically and automatically processes the image data to determine the orientation of the sample tube 162. If the sample tube 162 is not properly oriented (e.g., the sample tube 162 is upside-down), the controller 50 may stop the automated procedure and/or issue an alert to the operator. If the sample tube 162 is properly oriented, the controller 50 will continue the procedure.

In some embodiments, in the pickup location, the ends 161D, 161E of the sample tube assembly 160 are also in the field of view FOV of the barcode reader 122. The barcode reader 122 will send image data corresponding to the shapes of the ends 161D, 161E to the controller 50. The controller 50 will process the image data to determine whether each of the end caps 168, 169 are properly mounted on the sample tube 162. In some embodiments, the controller 50 programmatically and automatically processes the image data to determine whether each of the end caps 168, 169 are properly mounted on the sample tube 162. If one or both of the end caps 168, 169 are not properly mounted on the sample tube 162, the controller 50 may stop the automated procedure and/or issue an alert to the operator. If both of the end caps 168, 169 are properly mounted on the sample tube 162, the controller 50 will continue the procedure.

The controller 50 will then operate the actuator 119 to extend the gripper 118, grab the selected sample tube assembly 160 with the gripper 118, and remove the sample tube assembly 160 from the carousel tray 112.

In some embodiments, the barcode 170 will be in the field of view FOV of the barcode reader 122 when the sample tube 162 is held in the gripper 118, and the barcode reader 122 will read the barcode 170 and send image data corresponding to the barcode 170 to the controller 50. The controller 50 will process the image data to determine the orientation of the sample tube 162. In some embodiments, the controller 50 programmatically and automatically processes the image data to determine the orientation of the sample tube 162. If the sample tube 162 is not properly oriented, the controller 50 may stop the automated procedure and/or issue an alert to the operator. If the sample tube 162 is properly oriented, the controller 50 will continue the procedure.

In some embodiments, the ends 161D, 161E of the sample tube assembly 160 are also in the field of view FOV of the barcode reader 122 when the sample tube 162 is held in the gripper 118, and the barcode reader 122 will acquire an image of the ends 161D, 161E of the sample tube assembly 160 and will send image data corresponding to the shapes of the ends 161D, 161E to the controller 50. The controller 50 will process the image data to determine whether each of the end caps 168, 169 is properly mounted on the sample tube 162. If one or both of the end caps 168, 169 is/are not properly mounted on the sample tube 162, the controller 50 may stop the automated procedure and/or issue an alert to the operator. If both of the end caps 168, 169 are properly mounted on the sample tube 162, the controller 50 will continue the procedure.

The controller 50 will then operate the actuator 119 to place the sample tube assembly 160 in the capping/decapping station 130. The capping/decapping station 130 will remove the end caps 168, 169 so that the sample tube 162 is held in the gripper 118 without the end caps 168, 169 thereon.

In some embodiments, after the decapping operation by the capping/decapping station 130 is executed, the barcode reader 122 and controller 50 may again cooperate to acquire an image of the ends 161D, 161E of the sample tube 162 and confirm that both of the end caps 168, 169 have been removed from the sample tube 162.

Following removal of the end caps 168, 169, the barcode reader 122 and controller 50 may again cooperate to read the barcode 170 and determine whether the sample tube 162 is properly oriented.

The controller 50 will operate the actuator 119 to place the decapped sample tube 162 in the sampling station 150. The sample 165 is then desorbed by the sampling station 150 from the sample tube 162 and transferred to the GC system as described above.

Using the robot arm 116, the controller 50 may then transport the sampling tube 162 to the capping/decapping station 130, where the end caps 168, 169 are reinstalled. Using the robot arm 116, the controller 50 may then return the sample tube assembly 160 to the carousel tray 112 or placed elsewhere. At each step, the barcode reader 122 and controller 50 may cooperate to determine the orientation of the sample tube 162 and the presence of the end caps 168, 169 on the sample tube 162 in the same manner as described above.

The sample analyzer system 10 and, in particular, the sample tube monitoring system 120, can prevent or risk problems associated with misorientation of the sample tube 162. As discussed above, each sample tube 162 has a prescribed directionality. If the sample tube 162 is installed in the sampling station 150 in the wrong orientation (e.g., with the outlet end 161E in the supply fixture 154 and the inlet end 161D in the outlet fixture 156), the reliability and/or accuracy of the analysis or measurement may be compromised, the sample may be lost, and/or the sample tube assembly 160 may be damaged.

The sample analyzer system 10 and, in particular, the sample tube monitoring system 120, can also prevent or risk problems associated with improper capping of the sample tube 162. If the sample tube 162 is installed in the capping/decapping station 130 to be decapped with one or both ends 163D, 163E of the sample tube 162 missing its cap, the capping/decapping station 130 may become jammed or otherwise damaged as a result. If the sampling tube 162 is installed in the sampling station 150 with one or both of the end caps 168, 169 still mounted on an end 163D, 163E of the sample tube 162, the sampling station 150 will not operate properly and may be damaged.

The sample tube monitoring system 120 may include one or more optical sensors 122 for reading the visible indicia 170 for determining the orientation of the sample tube 162, and one or more additional optical sensors for determining whether one or both of the end caps 168, 169 are mounted on the ends of the sample tube 162.

Operations described herein can be executed by or through the controller 50. The actuators 115, 119 and other devices of the system 10 can be electronically controlled. According to some embodiments, the controller 50 programmatically executes some, and in some embodiments all, of the steps described. According to some embodiments, the movements of the actuators 115, 119 are fully automatically and programmatically executed by the controller 50.

In some embodiments, the controller 50 programmatically and automatically executes each of the steps of reading the barcode 170, processing the image data to determine the orientation of the sample tube 162, issuing an alert or stopping processing of the sample tube 162, if necessary, and placing the sample tube 162 in the sampling station 150. In some embodiments, the controller 50 programmatically and automatically executes each of the steps of acquiring an image of the ends of the sample tube 162, determining whether the end caps 168, 169 are or are not mounted thereon, and issuing an alert or stopping processing of the sample tube 162, if necessary. In some embodiments, the controller 50 programmatically and automatically executes each of the steps of transporting the sample tube 162 from the carousel tray 112 to the sampling station 150. In some embodiments, the controller 50 programmatically and automatically executes each of the steps of operation of the ATD device 100 described above.

Embodiments of the controller 50 logic may take the form of an entirely software embodiment or an embodiment combining software and hardware aspects, all generally referred to herein as a "circuit" or "module." In some embodiments, the circuits include both software and hardware and the software is configured to work with specific hardware with known physical attributes and/or configurations. Furthermore, controller logic may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Figure 7:
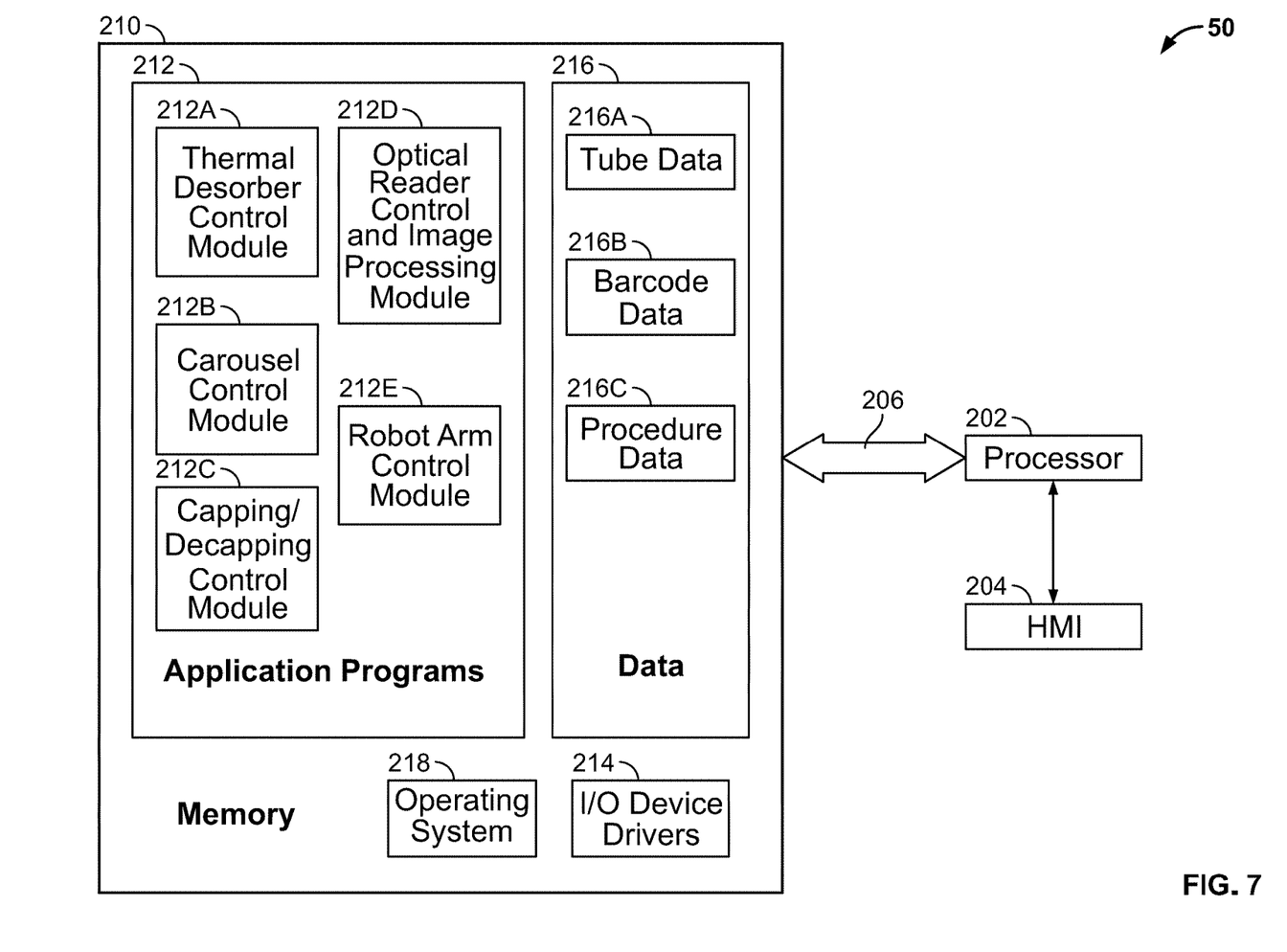
FIG. 7 is a schematic diagram representing a controller forming a part of the sample analyzer system of FIG. 1.

FIG. 7 is a schematic illustration of a circuit or data processing system that can be used in the controller 50. The circuits and/or data processing systems may be incorporated in a digital signal processor 202 in any suitable device or devices. The processor 202 communicates with the HMI 204 and memory 210 via an address/data bus 206. The processor 202 can be any commercially available or custom microprocessor. The memory 210 is representative of the overall hierarchy of memory devices containing the software and data used to implement the functionality of the data processing system. The memory 210 can include, but is not limited to, the following types of devices: cache, ROM, PROM, EPROM, EEPROM, flash memory, SRAM, and DRAM.

FIG. 7 illustrates that the memory 210 may include several categories of software and data used in the data processing system: the operating system 218; the application programs 212; the input/output (I/O) device drivers 214; and data 216.

The data 216 can include equipment-specific data. FIG. 7 also illustrates that the data 216 can include tube data 216A, barcode data 216B and procedure data 216C. The tube data 216A can include data relating to or representing characteristics of each sample tube 162, including a unique identifier (e.g., serial number), name, and description of an analyte contained in the sample tube 162, for example. The barcode data 216B can include a registry indexing or cross-referencing barcodes to the serial numbers of the sample tubes 162, for example. The procedure data 216C can include data representing a protocol or sequence of steps to execute the procedures described herein (including an analytical sequence, for example).

FIG. 7 also illustrates that application programs 212 can include a thermal desorber control module 212A (to control the TD system 140), a carousel control module 212B (to control the actuator 115), a capping/decaping control module 212C (to control the capping/decapping station 130), an optical reader control and image processing module 212D (to control the sample tube monitoring system 120 (including the optical sensor 122)), and a robot arm control module 212E (to control the actuator(s) 119).

As will be appreciated by those of skill in the art, the operating system 218 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 214 typically include software routines accessed through the operating system 218 by the application programs 212 to communicate with devices such as I/O data port(s), data storage and certain memory components. The application programs 212 are illustrative of the programs that implement the various features of the data processing system and can include at least one application, which supports operations according to embodiments of the present technology. Finally, the data 216 represents the static and dynamic data used by the application programs 212, the operating system 218, the I/O device drivers 214, and other software programs that may reside in the memory 210.

As will be appreciated by those of skill in the art, other configurations may also be utilized while still benefiting from the teachings of the present technology. For example, one or more of the modules may be incorporated into the operating system, the I/O device drivers or other such logical division of the data processing system. Thus, the present technology should not be construed as limited to the configuration of FIG. 7, which is intended to encompass any configuration capable of carrying out the operations described herein. Further, one or more of the modules can communicate with or be incorporated totally or partially in other components, such as the controller 50.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. An automated thermal desorption system including:
a sample tube including a chamber to contain an analyte;
visible indicia on the sample tube; and
an automated thermal desorption device including:
a sampling station configured to receive the sample tube and including a heating device, wherein the heating device is configured to heat the sample tube in the sampling station and thereby desorb the analyte from the sample tube;
a tube transport system including a sample tube holder configured to hold a plurality of the sample tubes, wherein the tube transport system is configured to programmatically and automatically move the sample tube from the sample tube holder to the sampling station; and
a sample tube monitoring system including:
an optical sensor configured to read the visible indicia on the sample tube in the automated thermal desorption device and to generate an output signal corresponding thereto; and
a controller configured to receive the output signal corresponding to the visible indicia from the optical sensor and to determine an orientation of the sample tube with respect to the automated thermal desorption device based on the output signal.

2. The automated thermal desorption system of claim 1 wherein the visible indicia is a barcode.

3. The automated thermal desorption system of claim 2 wherein the barcode is substantially permanently located on the sample tube.

4. The automated thermal desorption system of claim 3 wherein the barcode is substantially permanently printed, etched or embossed on the sample tube.

5. The automated thermal desorption system of claim 1 wherein the controller is configured to programmatically and automatically determine whether the sample tube is not oriented in a prescribed orientation with respect to the automated thermal desorption device.

6. The automated thermal desorption system of claim 1 wherein the sample tube monitoring system is configured to:
determine that the sample tube is not oriented in a prescribed orientation with respect to the automated thermal desorption device; and
in response to determining that the sample tube is not oriented in the prescribed orientation, automatically stop processing of the sample tube by the automated thermal desorption device.

7. The automated thermal desorption system of claim 1 wherein:
the sampling station includes an outlet conduit;
the sampling station is configured to receive the sample tube such that the chamber is fluidly connected to the outlet conduit and the sample tube is positioned to be heated by the heating device;
when the sample tube is disposed in the sampling station, the sample tube is heated by the heating device and the analyte is desorbed from the sample tube and flowed from the sample tube and into the outlet conduit; and
the sample tube monitoring system is configured to read the visible indicia using the optical sensor when the sample tube is in the sampling station and to determine therefrom an orientation of the sample tube with respect to the sampling station.

8. The automated thermal desorption system of claim 7 wherein:
the automated thermal desorption device further includes an inlet conduit fluidly connected to a supply of a carrier gas; and
the sampling station is configured to receive the sample tube such that the chamber is fluidly connected to the inlet conduit to direct a flow of the carrier gas from the inlet conduit, through the chamber and into the outlet conduit.

9. The automated thermal desorption system of claim 1 wherein:
the sample tube monitoring system is configured to read the visible indicia using the optical sensor when the sample tube is in the sample tube holder and to determine therefrom an orientation of the sample tube with respect to the automated thermal desorption device.

10. The automated thermal desorption system of claim 9 wherein the sample tube holder is a rotatable carousel.

11. The automated thermal desorption system of claim 1 wherein:
the sampling station includes an outlet conduit;
the sampling station is configured to receive the sample tube such that the chamber is fluidly connected to the outlet conduit and the sample tube is positioned to be heated by the heating device;
the tube transport system includes a robot arm, wherein the tube transport system is configured to collect and move the sample tube to the sampling station using the robot arm; and
when the sample tube is disposed in the sampling station, the sample tube is heated by the heating device and the analyte is desorbed from the sample tube and flowed from the sample tube and into the outlet conduit; and
the optical sensor is mounted on the robot arm.

12. The automated thermal desorption system of claim 1 including an end cap mounted on the sample tube and selectively removable from the sample tube, wherein the sample tube monitoring system is configured to acquire an image of the sample tube using the optical sensor and to determine therefrom whether the end cap is mounted on the sample tube.

13. The automated thermal desorption system of claim 12 wherein the sample tube monitoring system is configured to automatically stop processing of the sample tube by the automated thermal desorption device based on a determination by the sample tube monitoring system that the end cap is not mounted on the sample tube.

14. The automated thermal desorption system of claim 12 wherein:
the automated thermal desorption device includes a decapping station configured to remove the end cap from the sample tube; and
the sample tube monitoring system is configured to, in response to determining that the end cap is not mounted on the sample tube, automatically stop the automated thermal desorption device from attempting to remove the end cap from the sample tube using the decapping station.

15. The automated thermal desorption system of claim 12 wherein:

the automated thermal desorption device includes a decapping station configured to remove the end cap from the sample tube; and the tube transport system is configured to programmatically and automatically move the sample tube from the sample tube holder to the decapping station and to the sampling station.

16. The automated thermal desorption system of claim 1 including a gas chromatograph fluidly connected to the automated thermal desorption device to receive and detect the desorbed analyte from the automated thermal desorption device.

17. The automated thermal desorption system of claim 1 wherein the controller is configured to receive the output signal corresponding to the visible indicia from the optical sensor and to determine the orientation of the sample tube with respect to the sampling station based on the output signal.

18. The automated thermal desorption system of claim 1 wherein the sample tube monitoring system is configured to read the visible indicia using the optical sensor after the sample tube is removed from the sample tube holder by the tube transport system, and to determine therefrom the orientation of the sample tube with respect to the automated thermal desorption device.

19. The automated thermal desorption system of claim 1 wherein the sample tube monitoring system is configured to read the visible indicia using the optical sensor at multiple different locations in the automated thermal desorption device.

20. The automated thermal desorption system of claim 19 wherein: the sample tube monitoring system is configured to read the visible indicia using the optical sensor when the sample tube is in the sample tube holder and to determine therefrom an orientation of the sample tube with respect to the automated thermal desorption device; and the sample tube monitoring system is configured to also read the visible indicia using the optical sensor after the sample tube is removed from the sample tube holder by the tube transport system and to determine therefrom the orientation of the sample tube with respect to the automated thermal desorption device.

21. The automated thermal desorption system of claim 1 wherein:

the automated thermal desorption device includes a support frame; and the sampling station, the sample tube holder, the tube transport system, and the sample tube monitoring system are mounted on the support frame.

22. A method for desorbing an analyte from a sample tube, the method comprising:

providing a sample tube including a chamber containing an analyte, wherein visible indicia is disposed on the sample tube;

providing an automated thermal desorption device including:

a sampling station configured to receive the sample tube and including a heating device;

a tube transport system including a sample tube holder configured to hold a plurality of the sample tubes; and a sample tube monitoring system including:

an optical sensor configured to read the visible indicia on the sample tube and to generate an output signal corresponding thereto; and a controller configured to receive the output signal corresponding to the visible indicia from the optical sensor;

reading the visible indicia using the optical sensor of the sample tube monitoring system in the automated thermal desorption device and determining an orientation of the sample tube with respect to the automated thermal desorption device based on the visible indicia using the controller;

using the tube transport system, moving the sample tube from the sample tube holder and placing the sample tube in the sampling station; and heating the sample tube in the sampling station and thereby desorbing the analyte from the sample tube.

23. An automated thermal desorption system including:

a sample tube including a chamber to contain an analyte;

an end cap mounted on the sample tube and selectively removable from the sample tube;

an automated thermal desorption device including:

a sampling station configured to receive the sample tube and including a heating device, wherein the heating device is configured to heat the sample tube in the sampling station and thereby desorb the analyte from the sample tube;

a decapping station configured to remove the end cap from the sample tube;

a tube transport system including a sample tube holder configured to hold a plurality of the sample tubes, wherein the tube transport system is configured to programmatically and automatically move the sample tube from the sample tube holder to the decapping station and to the sampling station; and a sample tube monitoring system including:

an optical sensor configured to acquire an image of the sample tube in the automated thermal desorption device; and a controller configured to receive image data corresponding to the acquired image from the optical sensor and to determine whether the end cap is mounted on the sample tube based on the acquired image.

24. The automated thermal desorption system of claim 23 wherein the end cap is a first end cap, and including a second end cap mounted on an end of the sample tube opposite the first end cap and selectively removable from the sample tube, wherein the controller is configured to determine whether the second end cap is mounted on the sample tube based on the acquired image.

25. The automated thermal desorption system of claim 23 wherein:

the sample tube monitoring system is configured to, in response to determining that the end cap is not mounted on the sample tube, automatically stop the automated thermal desorption device from attempting to remove the end cap from the sample tube using the decapping station.

26. The automated thermal desorption system of claim 25 wherein:

the sample tube monitoring system is configured to acquire a second image of the sample tube to confirm that that the end cap has been removed from the sample tube by the decapping station and:

if the sample tube monitoring system determines that the end cap is still mounted on the sample tube, automatically stop the tube transport system from moving the sample tube to the sampling station; and if the sample tube monitoring system determines that the end cap is no longer mounted on the sample tube, permit the tube transport system to move the sample tube to the sampling station.

27. The automated thermal desorption system of claim 23 wherein:
the sample tube monitoring system is configured to acquire an image of the sample tube to confirm that that the end cap has been removed from the sample tube by the decapping station and:
if the sample tube monitoring system determines that the end cap is still mounted on the sample tube, automatically stop the tube transport system from moving the sample tube to the sampling station; and
if the sample tube monitoring system determines that the end cap is no longer mounted on the sample tube, permit the tube transport system to move the sample tube to the sampling station.

28. A method for desorbing an analyte from a sample tube, the method comprising:
providing a sample tube including a chamber containing an analyte;
providing an automated thermal desorption device including:
a sampling station configured to receive the sample tube and including a heating device;
a decapping station configured to remove an end cap from the sample tube;
a tube transport system including a sample tube holder configured to hold a plurality of the sample tubes; and
a sample tube monitoring system including:
an optical sensor configured to acquire an image of the sample tube in the automated thermal desorption device; and
a controller configured to receive image data corresponding to the acquired image from the optical sensor and to determine whether the end cap is mounted on the sample tube based on the acquired image;
acquiring an image of the sample tube in the automated thermal desorption device using the optical sensor of the sample tube monitoring system and determining whether the end cap is mounted on the sample tube based on the acquired image using the controller;
moving the sample tube from the sample tube holder to the decapping station using the tube transport system;
removing the end cap from the sample tube using the decapping station;
moving the sample tube from the decapping station to the sampling station using the tube transport system; and
heating the sample tube in the sampling station and thereby desorbing the analyte from the sample tube.

* * * * *

UNITED STATES PATENT AND TRADEMARK OFFICE
CERTIFICATE OF CORRECTION

PATENT NO. : 10,598,637 B2
APPLICATION NO. : 15/653173
DATED : March 24, 2020
INVENTOR(S) : Tolley et al.

Page 1 of 1

It is certified that error appears in the above-identified patent and that said Letters Patent is hereby corrected as shown below:

In the Claims

Column 15, Line 33, Claim 20:
Please insert a new paragraph between the words "wherein:" and "the sample"

Column 15, Line 37, Claim 20:
Please insert a new paragraph between the words "device; and" and "the sample"

Column 16, Line 62, Claim 26:
Please correct "that that the end cap" to read -- that the end cap --

Column 17, Line 8, Claim 27:
Please correct "confirm that that" to read -- confirm that --

Signed and Sealed this
Fourth Day of August, 2020

Andrei Iancu
*Director of the United States Patent and Trademark Office*